United States Patent [19]

Brechot et al.

[11] Patent Number: 5,849,508

[45] Date of Patent: Dec. 15, 1998

[54] PROCESS FOR THE DETECTION OF CELL PROLIFERATION BY DETECTING HUMAN CYCLIN A

[75] Inventors: Christian Brechot; Jian Wang; Xavier Chenivesse; Berthold Henglein; Frédérique Zindy, all of Paris Cedex, France

[73] Assignee: Institut National de la Sante et de la Recherche Medicale, Paris, Cedex, France

[21] Appl. No.: 460,895

[22] Filed: Jun. 5, 1995

Related U.S. Application Data

[62] Division of Ser. No. 368,403, Jan. 3, 1995, which is a continuation of Ser. No. 650,805, Feb. 6, 1991, abandoned.

[30] Foreign Application Priority Data

Feb. 12, 1990 [FR] France ................................ 90 01596

[51] Int. Cl.⁶ ..................... G01N 33/574; G01N 33/53; G01N 33/567
[52] U.S. Cl. ..................... 435/7.23; 435/7.1; 435/7.21; 530/387.1; 530/388.1
[58] Field of Search .................................. 435/7.1, 7.21, 435/7.23; 530/350, 387.1, 388.1

[56] References Cited

PUBLICATIONS

Carbonaro–Hall et al Oncogene 8(6):1749–59 (1993).
Swenson et al. Cell 47:861–70 (1986).
Giordano et al. Cell 58:981–90 (1989).
Pines et al Nature 346:760–63 (1990).

*Primary Examiner*—Lila Feisee
*Assistant Examiner*—Ray F. Ebert
*Attorney, Agent, or Firm*—Larson & Taylor

[57] ABSTRACT

The invention is directed generally to a DNA sequence coding for human cyclin A and in particular to antibodies, or antisera including such antibodies, which bind to human cyclin A as encoded by the sequence of SEQ ID NO: 1 and which are useful in detecting cellular proliferation. The antibodies of the invention can be polyclonal or monoclonal, and are preferably generated by injection of purified human cyclin A into an animal host. The invention is particularly advantageous because it has been discovered that the gene encoding for human cyclin A is a site for integration of the hepatitis B virus associated with hepatocellular carcinoma, and by detecting human cyclin A through the use of the antibodies of the invention, one can detect and diagnose cell proliferation. Through the use of the present invention, cell proliferation and tumorigenesis can thus be detected at early stages, and such conditions can then be treated or inhibited by the use of anti-sense human cyclin A DNA.

9 Claims, 3 Drawing Sheets

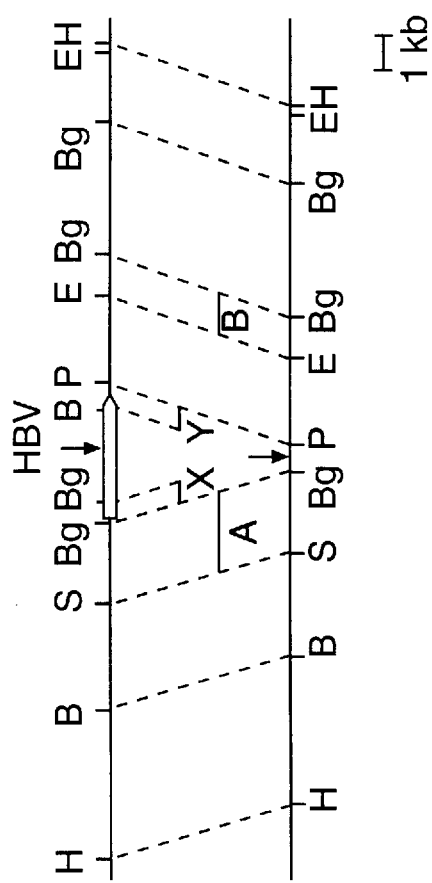
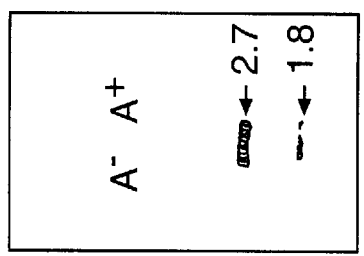
FIG. 1A
FIG. 1B
FIG. 1C (194) MRCILVDWLVEVSEEYKLHRETLFLGVNYIDRFLSKISVLRGKLQLVGAA CLAM A
(208) MRAILVDWLVEVGEEYKLQNETLHLAVNYIDRFLSSMVLRGKLQLVGTA HUMAN A
(234) MRSILIDWLVEVSEEYKLDTETLYLSVFYLDRFLSQMAVVRSKLQLVGTA DROSOPHILIA A (244) SMFLAAKYEEIYPPDVKEFAYITDDTYTSQQVLRMEHLILKVLTFDVAVP CLAM A
(258) AMLLASKFEEIYPPEVAEFVYITDDTYTKKQVLRMEHLVKVLTFDLAAP HUMAN A
(284) AMYIAAKYEEIYPPEVGEFVFLTDDSYTKAQVLRMEQVILKILSFDLCTP DROSOPHILIA A (294) TTNWF-CEDFLKSCDADDKLKSLTMFLTELTLIDMDAYLKYLPSITAAAA CLAM A
(308) TVNQFLTQYFLHQQPANCKVESLAMFLGELSLIDADPYLKYLPSVIAGAA HUMAN A
(334) TAYVF-INTYAVLCDMPEKLKYMTLYISELSLMEGETYLQYLPSLMSSAS DROSOPHILIA A

FIG. 2A

```
(200) MRAILIDWLVQVQMKFRLLQETMYMTVSIIDRFMQNNCVPKKMLQLVGVT  HUMAN B
         *  **  *       *
(208) MRAILVDWLVEVGEEYKLQNETLHLAVNYIDRFLSSMSVLRGKLQLVGTA  HUMAN A
       *                 *
(198) MRAILIDWLCQVHHRFHLLQETLYLTVAIIDRLLQESPVPRNKLQLVGVT  CLAM B (250) AMFIASKYEEMYPPEIGDFAFVTDNTYTKHQIRQMEMKILRALNFGLGRP  HUMAN B
         *    *        ***           *   ***
(258) AMLLASKFEEIYPPEVAEFVYITDDTYTKKQVLRMEHLVLKVLTFDLAAP  HUMAN A
       *                *                    *
(248) SMLIASKYEEMYAPEVADFVYISDNAYTKKEILEMEQHILKKLNFSFGRP  CLAM B (300) LPLHFLRRASKIGEVDVEQ-HTLAKYLMELTMLD-YDMVHFPPSQIAAGA  HUMAN B
         *                *            **   
(308) TVNQFLTQYFLHQQPANCKVESLAMFLGELSLIDADPYLKYLPSVIAGAA  HUMAN A
       *                *            *  ***  *
(298) LCLHFLRRDSKAGQVDANK-HTLAKYLMELTTE-YDMVQYLPSKIAAAA  CLAM B
```

FIG. 2B

SEQUENCE LISTING ( 1 ) GENERAL INFORMATION:

( i i i ) NUMBER OF SEQUENCES: 1

( 2 ) INFORMATION FOR SEQ ID NO:1 :

( i ) SEQUENCE CHARACTERISTICS:
        ( A ) LENGTH: 1634 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: HOMO SAPIENS ( i x ) FEATURE:
        ( A ) NAME/KEY: Human cyclin A
        ( B ) LOCATION: coding sequence from base 97 to base 1392,
            coding for a protein of 432 amino acids.

( x i ) SEQUENCE DESCRIPTION: SEQ ID NO:1:

```
TATTCTTTGG  CCGGGTCGGT  GCGAGTGGTC  GGCTGGGCAG  AGTGCACGCT              50

GCTTGGCGCC  GCACGGTGAT  CCCGCCGTCC  ACTCCGGGA   GCAGTG                  96
```

-continued

| | | | | | | | | | | | | | | | |
|---|---|---|---|---|---|---|---|---|---|---|---|---|---|---|---|
| ATG | TTG | GGC | AAC | TCT | GCG | CCG | GGG | CCT | GCG | ACC | CGC | GAG | | | 135 |
| MET | Leu | Gly | Asn | Ser | Ala | Pro | Gly | Pro | Ala | Thr | Arg | Glu | | | |
| 1 | | | | 5 | | | | | 10 | | | | | | |
| GCG | GGC | TCG | GCG | CTG | CTA | GCA | TTG | CAG | CAG | ACG | GCG | CTC | CAA | GAG | 180 |
| Ala | Gly | Ser | Ala | Leu | Leu | Ala | Leu | Gln | Gln | Thr | Ala | Leu | Gln | Glu | |
| | 15 | | | | 20 | | | | | 25 | | | | | |
| GAC | CAG | GAG | AAT | ATC | AAC | CCG | GAA | AAG | GCA | GCG | CCC | GTC | CAA | CAA | 225 |
| Asp | Gln | Glu | Asn | Ile | Asn | Pro | Glu | Lys | Ala | Ala | Pro | Val | Gln | Gln | |
| | 30 | | | | 35 | | | | | 40 | | | | | |
| CCG | CGG | ACC | CGG | GCC | GCG | CTG | GCG | GTA | CTG | AAG | TCC | GGG | AAC | CCG | 270 |
| Pro | Arg | Thr | Arg | Ala | Ala | Leu | Ala | Val | Leu | Lys | Ser | Gly | Asn | Pro | |
| | 45 | | | | 50 | | | | | 55 | | | | | |
| CGG | GGT | CTA | GCG | CAG | CAG | CAG | AGG | CCG | AAG | ACG | AGA | CGG | GTT | GCA | 315 |
| Arg | Gly | Leu | Ala | Gln | Gln | Gln | Arg | Pro | Lys | Thr | Arg | Arg | Val | Ala | |
| | 60 | | | | 65 | | | | | 70 | | | | | |
| CCC | CTT | AAG | GAT | CTT | CCT | GTA | AAT | GAT | GAG | CAT | GTC | ACC | GTT | CCT | 360 |
| Pro | Leu | Lys | Asp | Leu | Pro | Val | Asn | Asp | Glu | His | Val | Thr | Val | Pro | |
| | 75 | | | | 80 | | | | | 85 | | | | | |
| CCT | TGG | AAA | GCA | AAC | AGT | AAA | CAG | CCT | GCG | TTC | ACC | ATT | CAT | GTG | 405 |
| Pro | Trp | Lys | Ala | Asn | Ser | Lys | Gln | Pro | Ala | Phe | Thr | Ile | His | Val | |
| | 90 | | | | 95 | | | | | 100 | | | | | |
| GAT | GAA | GCA | GAA | AAA | GAA | GCT | CAG | AAG | AAG | CCA | GCT | GAA | TCT | CAA | 450 |
| Asp | Glu | Ala | Glu | Lys | Glu | Ala | Gln | Lys | Lys | Pro | Ala | Glu | Ser | Gln | |
| | 105 | | | | 110 | | | | | 115 | | | | | |
| AAA | ATA | GAG | CGT | GAA | GAT | GCC | CTG | GCT | TTT | AAT | TCA | GCC | ATT | AGT | 495 |
| Lys | Ile | Glu | Arg | Glu | Asp | Ala | Leu | Ala | Phe | Asn | Ser | Ala | Ile | Ser | |
| | 120 | | | | 125 | | | | | 130 | | | | | |
| TTA | CCT | GGA | CCC | AGA | AAA | CCA | TTG | GTC | CCT | CTT | GAT | TAT | CCA | ATG | 540 |
| Leu | Pro | Gly | Pro | Arg | Lys | Pro | Leu | Val | Pro | Leu | Asp | Tyr | Pro | MET | |
| | 135 | | | | 140 | | | | | 145 | | | | | |
| GAT | GGT | AGT | TTT | GAG | TCA | CCA | CAT | ACT | ATG | GAC | ATG | TCA | ATT | GTA | 585 |
| Asp | Gly | Ser | Phe | Glu | Ser | Pro | His | Thr | MET | Asp | MET | Ser | Ile | Val | |
| | 150 | | | | 155 | | | | | 160 | | | | | |
| TTA | GAA | GAT | GAA | AAG | CCA | GTG | AGT | GTT | AAT | GAA | GTA | CCA | GAC | TAC | 630 |
| Leu | Glu | Asp | Glu | Lys | Pro | Val | Ser | Val | Asn | Glu | Val | Pro | Asp | Tyr | |
| | 165 | | | | 170 | | | | | 175 | | | | | |
| CAT | GAG | GAT | ATT | CAC | ACA | TAC | CTT | AGG | GAA | ATG | GAG | GTT | AAA | TGT | 675 |
| His | Glu | Asp | Ile | His | Thr | Tyr | Leu | Arg | Glu | MET | Glu | Val | Lys | Cys | |
| | 180 | | | | 185 | | | | | 190 | | | | | |
| AAA | CCT | AAA | GTG | GGT | TAC | ATG | AAG | AAA | CAG | CCA | GAC | ATC | ACT | AAC | 720 |
| Lys | Pro | Lys | Val | Gly | Tyr | MET | Lys | Lys | Gln | Pro | Asp | Ile | Thr | Asn | |
| | 195 | | | | 200 | | | | | 205 | | | | | |
| AGT | ATG | AGA | GCT | ATC | CTC | GTG | GAC | TGG | TTA | GTT | GAA | GTA | GGA | GAA | 765 |
| Ser | MET | Arg | Ala | Ile | Leu | Val | Asp | Trp | Leu | Val | Glu | Val | Gly | Glu | |
| | 210 | | | | 215 | | | | | 220 | | | | | |
| GAA | TAT | AAA | CTA | CAG | AAT | GAG | ACC | CTG | CAT | TTG | GCT | GTG | AAC | TAC | 810 |
| Glu | Tyr | Lys | Leu | Gln | Asn | Glu | Thr | Leu | His | Leu | Ala | Val | Asn | Tyr | |
| | 225 | | | | 230 | | | | | 235 | | | | | |
| ATT | GAT | AGG | TTC | CTG | TCT | TCC | ATG | TCA | GTG | CTG | AGA | GGA | AAA | CTT | 855 |
| Ile | Asp | Arg | Phe | Leu | Ser | Ser | MET | Ser | Val | Leu | Arg | Gly | Lys | Leu | |
| | 240 | | | | 245 | | | | | 250 | | | | | |
| CAG | CTT | GTG | GGC | ACT | GCT | GCT | ATG | CTG | TTA | GCC | TCA | AAG | TTT | GAA | 900 |
| Gln | Leu | Val | Gly | Thr | Ala | Ala | MET | Leu | Leu | Ala | Ser | Lys | Phe | Glu | |
| | 255 | | | | 260 | | | | | 265 | | | | | |
| GAA | ATA | TAC | CCC | CCA | GAA | GTA | GCA | GAG | TTT | GTG | TAC | ATT | ACA | GAT | 945 |
| Glu | Ile | Tyr | Pro | Pro | Glu | Val | Ala | Glu | Phe | Val | Tyr | Ile | Thr | Asp | |
| | 270 | | | | 275 | | | | | 280 | | | | | |
| GAT | ACC | TAC | ACC | AAG | AAA | CAA | GTT | CTG | AGA | ATG | GAG | CAT | CTA | GTT | 990 |
| Asp | Thr | Tyr | Thr | Lys | Lys | Gln | Val | Leu | Arg | MET | Glu | His | Leu | Val | |
| | 285 | | | | 290 | | | | | 295 | | | | | |

| | | | | | | | | | | | | | | |
|---|---|---|---|---|---|---|---|---|---|---|---|---|---|---|
| TTG Leu 300 | AAA Lys | GTC Val | CTT Leu | ACT Thr | TTT Phe | GAC Asp 305 | TTA Leu | GCT Ala | GCT Ala | CCA Pro | ACA Thr 310 | GTA Val | AAT Asn | CAG Gln | 1035 |
| TTT Phe | CTT Leu 315 | ACC Thr | CAA Gln | TAC Tyr | TTT Phe | CTG Leu 320 | CAT His | CAG Gln | CAG Gln | CCT Pro | GCA Ala 325 | AAC Asn | TGC Cys | AAA Lys | 1080 |
| GTT Val | GAA Glu 330 | AGT Ser | TTA Leu | GCA Ala | ATG MET | TTT Phe 335 | TTG Leu | GGA Gly | GAA Glu | TTA Leu | AGT Ser 340 | TTG Leu | ATA Ile | GAT Asp | 1125 |
| GCT Ala | GAC Asp 345 | CCA Pro | TAC Tyr | CTC Leu | AAG Lys | TAT Tyr 350 | TTG Leu | CCA Pro | TCA Ser | GTT Val | ATT Ile 355 | GCT Ala | GGA Gly | GCT Ala | 1170 |
| GCC Ala | TTT Phe 360 | CAT His | TTA Leu | GCA Ala | CTC Leu | TAC Tyr 365 | ACA Thr | GTC Val | ACG Thr | GGA Gly | CAA Gln 370 | AGC Ser | TGG Trp | CCT Pro | 1215 |
| GAA Glu | TCA Ser 375 | TTA Leu | ATA Ile | CGA Arg | AAG Lys | ACT Thr 380 | GGA Gly | TAT Tyr | ACC Thr | CTG Leu | GAA Glu 385 | AGT Ser | CTT Leu | AAG Lys | 1260 |
| CCT Pro | TGT Cys 390 | CTC Leu | ATG MET | GAC Asp | CTT Leu | CAC His 395 | CAG Gln | ACC Thr | TAC Tyr | CTC Leu | AAA Lys 400 | GCA Ala | CCA Pro | CAG Gln | 1305 |
| CAT His | GCA Ala 405 | CAA Gln | CAG Gln | TCA Ser | ATA Ile | AGA Arg 410 | GAA Glu | AAG Lys | TAC Tyr | AAA Lys | AAT Asn 415 | TCA Ser | AAG Lys | TAT Tyr | 1350 |
| CAT His | GGT Gly 420 | GTT Val | TCT Ser | CTC Leu | CTC Leu | AAC Asn 425 | CCA Pro | CCA Pro | GAG Glu | ACA Thr | CTA Leu 430 | AAT Asn | CTG Leu | TAA | 1395 |
| CAATGAAAGA | | CTGCCTTTGT | | TTTCTAAGAT | | | GTAAATCACT | | | CAAAGTATAT | | | | | 1445 |
| GGTGTACAGT | | TTTTAACTTA | | GGTTTTAATT | | | TTACAATCAT | | | TTCTGAATAC | | | | | 1495 |
| AGAAGTTGTG | | GCCAAGTACA | | AATTATGGTA | | | TCTATTACTT | | | TTTAAATGGT | | | | | 1545 |
| TTTAATTTGT | | ATATCTTTTG | | TATATGTATC | | | TGTCTTAGAT | | | ATTTGGCTAA | | | | | 1595 |
| TTTTAAGTGG | | TTTTGTTAAA | | GTATTAATGA | | | TGCCAGCTG | | | | | | | | 1634 |

PROCESS FOR THE DETECTION OF CELL PROLIFERATION BY DETECTING HUMAN CYCLIN A

This application is a division of application Ser. No. 08/368,403 filed Jan. 3, 1995, which is a continuation of application Ser. No. 07/650,805, filed Feb. 6, 1991, now abandoned.

This invention relates to new compositions containing in a high concentration and/or in a high purity a human cyclin A, said compositions being potentially useful notably for the preparation of detecting agents for cyclin, such as notably antisera or antibodies,whether they be monoclonal or not. The invention also relates to a process allowing one to prepare these compositions.

The invention also relates to a nucleotide sequence coding for human cyclin A as well as expression vectors incorporating this sequence in order to express the cyclin A, and a process for preparing cyclin A and compositions containing cyclin A through expression of these vectors.

The invention also relates to a process and agents for the detection or diagnosis of cell proliferation.

Finally, the invention relates to a process and agents for inhibiting cell proliferation.

It is known that chronic infection with the hepatitis B virus (HBV) is a risk factor for the development of hepatocellular carcinoma (22–24) and it has been established that the HBV virus's proviral DNA frequently integrates in the genome of human tumor cells from primary liver cancer (1–4). However, the part played by this integration in liver carcinogenesis is not yet fully understood and evidence of a direct part played by the virus in the cell transformation is scarce. More particularly, the effects of viral DNA integration in the cell genome are open to controversy. The woochuck hepatitis virus (WHV) often appears to act through deregulation of MYC after viral insertion (25). In man, the integration of HBV frequently induces, apparently in a non specific manner, deletions and translocations (3, 26–28). It has however been suggested that the integration on chromosome 11 (3) as well as rearrangement on a locus of chromosome 4q (29, 30) happen in a non random manner. The integration of HBV near a cell gene has been demonstrated only in a tumor in which the viral DNA has interrupted the region encoding for the retinoic acid beta receptor (31, 32).

The invention has allowed one to establish the existence of an individual site for integration of the HBV virus DNA in the human genome (chromosome 4q27) and more precisely in a gene encoding for/a human cyclin A whose existence was discovered simultaneously, and that this integration was present in liver cells at an early stage of tumor development without a notable chromosome rearrangement, showing none of the histological characteristics of chronic hepatitis or cirrhosis, in a clonal proliferation of a cell containing only one HBV integration, and was absent in the adjacent liver tissue, so that it is more than likely, through the resulting disturbance of the cyclin A function, that this insertion plays a direct part in liver carcinogenesis.

The inventors have moreover discovered that the expression of cyclin A (mRNA and protein) appeared during step S and step G2/M of the cell cycle and was associated with cell division. Therefore, they found in a rat livers during regeneration after partial hep/tectomy leading to a synthesis of cell DNA in a high proportion of hepatocytes, a maximum expression of cyclin A (mRNA and protein) during the synthesis step S of the cell DNA.

In the same way, the inventors found that the expression of cyclin A was at a maximum in upper leucocyte myeloblastic acute leukemia with quick doubling time and was very weak in the primitive liver cancer for which the doubling time of the tumor is slow.

The inventors also discovered that it was possible to block the synthesis of cyclin A in hepatocytes with the help of an anti-sense human cyclin A DNA.

According to the invention, the DNA corresponding to the insertion locus was cloned and sequenced and expression vectors allowing the production of a large amount of encoded cyclin A were built, and the object of the invention is thus a process for preparing human cyclin A through genetic expression as well as new compositions with a concentrated human cyclin A content and at a high purity degree.

One object of the invention is achieved in the isolation of a nucleotide sequence encoding for human cyclin A and vectors containing and/or expressing the sequence encoding for cyclin A.

Another objection of the invention is achieved in the sequence designated by SEQ ID NO: 1 in the attached sequence listing.

This sequence may be associated with other usual sets such as promoters, initiation or stop signals or introns or other non encoding sequences at the 3' and/or 5' end. It also includes variants notably obtained through substitution of codons or nucleotides preserving the meaning of the code,or through substitutions, insertions or deletions and encoding for an equivalent polypeptide and notably preserving the polypeptide's antigenicity. It also includes any fragment allowing the expression of a polypeptide preserving this antigenicity. Finally, the sequence also includes the human cyclin A gene, possibly incorporating some or all of the elements of an operon, and without natural flanking sequences, and any fragment allowing the expression of a polypeptide preserving an antigenicity of cyclin A.

Another object of the invention is moreover a detection process allowing the diagnosis of cell proliferation, in which the level of human cyclin A in the affected cells is determined, notably with the help of polyclonal antibodies, for example, animal antisera which are induced by immunization with human cyclin A or polyclonal antibodies as obtained by expression of the human cyclin A protein in bacterial systems, or monoclonal antibodies antihuman cyclin A.

An object of the invention is thus also these antibodies.

Another object of the invention is a process for treating cell proliferation, in which this proliferation is inhibited with the help of anti-sense human cyclin A cDNA. This cDNA concept also includes the relevant fragments of the cDNA sequence.

In order to ensure its introduction in the cell to be treated, this cDNA may notably be either included in a retroviral vector (for example according to the methods described by J. A. Wolff et al., Proc. Natl. Acad. Sci. 84:3344, 1987 or by D. G. Miller et al., Mol. Cell. Biol. 10:4239, 1990), or carried by a desialilated protein which may be attached on a receptor which is itself carried by the target cell in view of the penetration of the cDNA in the cell, with the cDNA and protein being notably linked by a polylysin (for example according to the methods described by G. Y. Wu & G. H. Wu, J. Biol. Chem. 263:14621, 1988 and by G. H. Wu et al., J. Biol. Chem. 264:16985, 1989), or included in a liposome.

An object of the invention is thus also the anti-sense cyclin A CDNA, the plasmids including this cDNA and the retroviral vectors which include it.

Another object of the invention is also the compound made up by the anti-sense cDNA in the desialilated protein, as well as the liposomes including the anti-sense cDNA.

Other advantages and features of the invention will appear from the following description given as a non-limiting example and referring to the appended drawing wherein:

FIG. 1A represents,
the restriction map of the HBV integration area in a tumor cell; the open box represents the 3.1 kb viral insert showing the virus orientation (+); the restriction sites are: B, Bam HI; Bg, Bgl II; E, Eco RI; H, Hind III; P, Pst I; S, Sst I;

sub-clones derived from tumor genome sequences as represented in A, all of them being devoid of repeating sequences; A is a 2.2 kb Sst I/Bgl II fragment; B is a 1.1 kb Eco RI/Bgl II fragment; the X (0.5 kb Bgl II) and Y (0.7 kb Bam HI/Pst I) fragments contain the recombination left and right sites; and the restriction map of
the HBV integration locus in its natural configuration; the arrow shows the viral integration site; the interrupted lines show identical restriction fragments;

FIG. 1B represents the virus-host linkage sequence in the locus;

FIG. 1C represents a Northern blot analysis of human new-born liver RNA after hybridization with clone B (line B of FIG. 1); A−: 50 μg poly A− RNA; A+: 5 μg poly A+ RNA; sizes are in kb.

FIG. 2 represents:
in A, an alignment for comparison of amino acids sequences from *S. solidissima* (Clam A) (4), *D. melanogaster* (Drosophila A) (5) and human cyclin A; the identical amino acids are linked with continuous lines and conservative substitutions are linked with an asterisk (*), in B, an alignment of cyclin sequences from *S. solidissima* (Clam) (15), cyclin B, human cyclin B (12) and human cyclin A.

I. DEMONSTRATION OF THE INSERTION

A well differentiated early primary hepatocellular carcinome (HCC) was analysed as developed in the form of a small nodule, isolated without accompanying cirrhosis in a woman having antibodies against hepatitis B surface antigen. The cell DNA was extracted according to the conventional methods from the tumor tissue on/the one hand, and from the non-tumoral adjacent tissue on the other hand. Southern blots of these DNAs were probed with HBV DNA. Whereas in the non tumoral tissue HBV DNA was only present in the form of free molecules, tumoral DNA formed a unique band corresponding to the integration of only one HBV genome copy per cell.

A tumoral DNA phage library was constructed and allowed the isolation of several overlapping clones which were identified with a specific HBV probe. The library was constructed by partial digestion of tumor DNA with Hind III and ligation in Hind III branches of phage L 47. A population of overlapping phage clones was isolated using cloned HBV as a probe. Sub-cloning was made with Bluescript (Stratagene) vectors. The natural allele (FIG. 1c) was cloned from an EMBL 3 library made of placental DNA which was partially digested with Sau 3A I. Sequencing was made by the method described in reference (39).cDNA was isolated from a library constructed from adult human liver mRNA primed with oligo(dT) (32).

The resulting restriction map of the HBV provirus and the flanking cell sequences in the tumor is represented in FIG. 1A. FIG. 1B shows sub-clones A, X, Y, B, without repeating sequences, which were derived from phage clones. The sequencing of fragments X et Y (FIG. 1B) of the provirus-host linkage, with detailed restriction analysis of the proviral insert, confirmed that a viral genome without major rearrangements was obtained. The virus-cells linkages were both situated in HBV end zones (nucleotides 1840 and 1617 in the viral core, and open reading frames X, respectively (1) (FIG. 1D)). Hybridization of Southern blots made up from tumor DNA with the A and B probes of FIG. 1B confirmed the genome configuration as represented in FIG. 1A. With probe B, or a 1.1 kb Eco RI/Bgl II fragment, a normal human genome phage library was scanned and several overlapping clones were isolated.

The restriction map of the area wherein HBV integration in its native configuration is made is represented in FIG. 1C. A comparison of restriction maps from FIGS. 1A and 1C shows that viral integration in a tumor did not produce any major rearrangements in its vicinity.

Hybridization of clone B with normal new-born liver polyadenylated and non polyadenylated RNA Northern blots allowed one to identify two 1.8 kb and 2.7 kb transcripted RNA polyadenylated molecules (FIG. 1E). Subsequent screening of a normal human liver cDNA phage library allowed one to isolate five cDNA clones which according to their restriction maps represent the same RNA molecule. The cDNA sequence of the largest (1641 bp) cloned insert is represented in the sequence listing SEQ ID NO: 1 showing an open reading frame (ORF) having a 431 amino acid protein coding capacity and a relative molecular mass Mr=47,954. In the reading frame of the conjectured AUG initiation codon is a stop codon in a 30 bp upstream position. The cDNA contains no poly A zone nor any polyadenylation consensus signal.

A comparative research made with the help of a computer has shown that the protein as derived from this insert contains a 150 amino acid region (aa position 209–358) for a cyclin box (9) which is the major preservation area of all known cyclins (4, 5, 7, 9, 12). Comparison for each alignment is represented on FIGS. 2A and 2B, and the protein has a wide similarity with A cyclins from *S. solidissima* (4) and *D. melanogaster* (5). In view of the fact that it has only 54 amino acid positions out of 150 which are common to the cyclin spaces of *S. solidissima* (1) and man (12), B cyclins, the derived protein is a human A cyclin. The N-terminal end of the protein does not show any notable homology with other known proteins, including other cyclins, which is a common feature of known cyclins.

It has turned out that fragment A (FIG. 1B) reacts through hybridization with the cDNA (FIG. 1). Fragments A and B were therefore partially sequenced and sequences were found starting from the 5' and 3' ends of cDNA, respectively. The orientation which is inferred from the cyclin A gene is from left to right on FIG. 1. A study of the sequence then shows that cyclin A has several exons and, because cell sequences of X,Y virus-host linkage fragments (FIG. 1B) are not to be found in the cDNA, it follows that integration of the HBV virus DNA is made in a gene intron.

Viral insertion in the thus discovered locus deregulates operation of the cyclin A gene, which seems to have decisive consequences on the regulation of cell growth. For more details on cyclins A and B, and their importance in mitosis, see 5–21, 33–38.

II. PRODUCTION OF HUMAN A CYCLIN THROUGH GENETIC EXPRESSION

The cloned cDNA molecule, as represented on the list, is inserted in a bacterial or preferably eukaryotic expression vector, for instance through cloning of the cDNA in the Bluescript cloning vector, insertion in the pET-3b expression plasmid vector, transfection of an host, for instance a bacterial host, the ends of the sequence being determined with the Eco RI and Sma I restriction enzyme. For a detailed description of this method, see: Gene-1987, 56: 125–135.

A cyclin A preparation may be obtained from the bacterial culture through gel purification.

III. A STUDY AF THE EXPRESSION OF THE CYCLIN A GENE IN HEPATOCYTES AND IN REGENERATING LIVER

The cDNA is used as a probe to study the expression of the A cyclin on cultivated hepatocytes and regenerating rat liver models.

Normal rat hepatocytes may be maintained in a primary culture during a period of about 10 days while preserving part of the hepatocyte's differentiated functions. However, there is no cell proliferation. One can stimulate DNA synthesis by adding to the medium some epidermal growth factor, EGF, pyruvate and insulin. A cell DNA synthesis (as measured by incorporation of tritiated thymidin) is obtained and is at a maximum on the third/day of culture. It appeared in Northern blot and Western blot studies that the RNA and cyclin A protein accumulation peaks are to be found during the DNA synthesis step (third day of culture after stimulation), as opposed to the B1 cyclin which is already detected on the first day of hepatocyte culture and is still to be found on the fifth day. Moreover, cyclin A is not detected in hepatocytes whose DNA synthesis was not stimulated (as opposed to cyclin B1).

In order to check that these in vitro observations reflected the true in vivo situation one used a regenerating rat liver model. After a two thirds hepatectomy, a first synchronous mitosis involving about 40% of hepatocytes appears. A cell DNA synthesis between hours twenty and twenty-four is followed about six hours later with the first mitosis. The important point is the more belated starting point of liver non-hepatocyte cell proliferation which will start about twenty-four hours after the proliferation of hepatocytes.

It appeared that:

cyclin A is not detected in a normal liver.

cyclin A is detected (RNA and protein) during the cell DNA synthesis step. Accumulation of cyclin A is followed by a slight decrease in the proportion of cyclin A, then by a new increase during mitosis.

There again, cyclin B1 has a very different profile, being detected in the normal liver, and with its proportion not increasing during step S.

IV. DETECTION OF CYCLIN A ON TISSUE SECTIONS AS OBTAINED BY BIOPSY

Starting with frozen sections, a fixation is made with PFA (paraformaldehyde)—PBS 4% during 20 minutes at 4° C. or with methanol during 10 minutes at −20° C., this is washed once with PBS then twice with Tris-HCl (pH 7.6).

Starting with sections included in paraffin, one proceeds to dewax with xylene, the sections are hydrated (from 100% alcohol to distilled water), and are then washed twice with Tris-HCl (pH 7.6).

The rest of the protocol is the following:

quick immersion in 1% BSA (bovine serum albumin) or Tris-HCl;

incubation with avidin, 15 minutes;

washing with Tris-HCl+immersion in BSA;

incubation with biotin, 15 minutes;

2 washings with Tris-HCl+immersion in BSA;

incubation with normal serum, 20 minutes;

elimination of excess serum;

incubation with a human anticyclin A antibody during one night at 4° C.;

2 washing with Tris-HCl+immersion in BSA;

incubation with a biotinylated revelation antibody, during 30 minutes;

2 washings with Tris-HCl+immersion in BSA;

incubation with the avidin-biotin complex, 30 minutes;

2 washings with Tris-HCl;

revelation with diamino-benzidin (DAB), 5 minutes in the dark;

washings with water;

coloring with hematoxilin;

dehydration in alcohols (up to 100%);

immersions in xylene;

reading.

Reading allows some quantification of the rate of cyclin A present in the tissue by counting the percentage of labeled cell cores. In the normal liver this percentage is below 1%. Rates reaching 80% have been observed in proliferating tissues.

V. A PROCESS FOR THE DETECTION OR DIAGNOSIS OF CELL PROLIFERATION

As applied to circulating cells, any well known method for detection by antibodies, notably ELISA and particularly ELISA sandwich, as applied to sample taking, may be used.

As applied to tissues, cyclin A is directly detected in tissues as is usually done with known proliferation diagnosis tools.

The preparation of anti-cyclin A antibodies may be made in rabbits by injecting cyclin A as obtained by gel purification in order to obtain a rabbit antiserum.

Detection with quantification of human cyclin A in tissues may then be made by Western blot or immunohistochemistry.

This detection may use a counting of labeled cell cores and a comparison of the rate as counted with the rate of a normal sample of the same tissue.

VI. INHIBITION OF CELL PROLIFERATION

In vitro microinjection in hepatocytes, as stimulated by insulin, pyruvate and EGF in a primary culture, of plasmids containing the cyclin A complementary DNA in an antisense situation under the control of SV40 virus regulating elements blocks the synthesis of cell DNA.

To ensure the in vivo inhibition of cell proliferation, notably tumoral cell proliferation one uses constructions to bring the anti-sense DNA inside the cell to be treated.

One may first use a retroviral vector (J. A. Wolff et al. & D. G. Miller et al., supra) including the anti-sense cDNA and capable of infecting the target cell and thus to insert the anti-sense cDNA in the genome of this cell. To do so the human cyclin A cDNA is inserted in an anti-sense position into a plasmid, notably the commercial PKC4 plasmid, with an appropriate promotor, for instance the SV40 virus promotor. The plasmids in which the DNA is well integrated in an anti-sense position are then selected with a restriction map before introduction of the cDNA and its promotor into the retrovirus.

One may also use a protein which is capable of binding to a receptor of the target cell. The anti-sense cDNA is then bound to a desialilated protein (G. Y. Wu & C. H. Wu, and C. H. Wu et al., see supra) through a polylysin. After binding to the target cell the cDNA is introduced into the cell cytoplasm wherein it is transcribed into an anti-sense RNA which will block cyclin A synthesis by hybridation on the cell RNA.

One may also use liposomes including the anti-sense cDNA.

REFERENCES

1. TIOLLAIS, P., POURCEL, C. & DEJEAN, A. Nature 317, 489–495(1985).
2. BRECHOT, C., POURCEL, C., LOLISE, A., RAIN, B. & TIOLLAIS, P. Nature 286, 533–535 (1980).
3. NAGAYA, T. et al. Genes and Development 1, 773–782 (1987).
4. YAGINUMA, K. et al. J.Virol. 61, 1808–1813(1987).
5. SWENSON, K. I., FARRELL, K. M. & RUDERMAN, J. V. Cell 47, 861–870(1986).
6. LEHNER, C. F. & O'FARRELL, P. Cell 56, 957–968 (1989).
7. STANDART, N., MINSHULL, J., PINES, J. & HUNT, T. Dev. Biol. 124, 248–258(1987).
8. MINSHULL, J., BLOW, J. J. & HUNT, T. Cell. 56, 947–956(1989).
9. MEIJER, L. et al. EMBO J. 8, 2275–2282(1989).
10. PINES, J. & HUNT, T. EMBO J. 6, 2987–2995(1987).
11. MURRAY, A. M. & KIRSCHNER, M. W. Nature 339, 275–286(1989).
12. PINES, J. & HUNTER, T. Cell 58, 833–846(1989).
13. SOLOMON, M., BOOHER, R., KIRSCHNER, M. & BEACH, D. Cell 54, 738–739(1988).
14. GOEBL, M. & BYERS, B. Cell 54, 739–740(1988).
15. WESTENDORF, J. M., SWENSON, K. I. & RUDERMAN, J. V. J. Cell. Biol. 108, 1431–1444(1989).
16. DRAETTA, G. et al. Cell 56, 829–838(1989).
17. BRIZUELA, L., DRAETTA, G. & BEACH, D. Proc. Natl. Acad. Sci. U.S.A. 86, 4362–4366(1989).
18. DRAETTA, C. & BEACH, D. Cell 54, 17–26(1989).
19. LABBE, J. C. et al. EMBO J. 8, 3053–3058(1989).
20. MORIA, A. O., DRAETTA, G., BEACH, D., WANG, J. Y. J. Cell 58, 193–203(1989).
21. GIORDANO, A. et al. Cell 58, 981–990(1989).
22. KEW, M. C. & POPPER, H. Sem. Liver Dis. 2, 136–146 (1984).
23. BEASLEY, R. P., HWANG L. Y. Sem. Liver Dis. 4, 113–121(1984).
24. SAGUMA, K. et al. Hepatology 8, 1642–1646(1984).
25. HSU, T. et al. Cell 55, 627–635(1988).
26. TOKINO, T. et al. J. Virol. 61, 3848–3854(1987).
27. HINO, O., OHTAKE, K. & ROGLER, C. E. J. Virol. 63, 2638–2643(1989).
28. ROGLER, C. E. et al. Science 230, 319–322(1985).
29. PASQUINELLI, C. et al. J. Virol. 62, 629–632(1988).
30. BLANQUET, V., GARREAU, F., CHENIVESSE, X., BRECHOT, C. & TURLEAU, C. Human Genetics 80, 274–276(1988).
31. DEJEAN, A., BOUGUELERET, L., CRZESCHIK, K.H. & TIOLLAIS, P. Nature 322, 70–72(1986).
32. DETHE, H., MARCHIO, A., TIOLLAIS, P. & DEJEAN, A. Nature 330, 667–670(1987).
33. MORGAN, D., KAPLAN, J. M., BISHOP, J. M. & VARMUS, H. E. Cell 57, 775–786(1989).
34. SHENOY, S. et al. Cell 57, 763–774(1989).
35. McVEY, D. et al. Nature 341, 503–507(1989).
36. BUCHKOVICH, K., DUFFY, L. A. & HARLOW, Ed. Cell 58, 1097–1105 (1989).
37. CHEN, P. L., SCULLY, P., SHEW, J. Y. L. & LEE, W. H. Cell 58, 1193–1198(1989).
38. DECAPRIO, J. A. et al. Cell 58, 1085–1095(1989).
39. SANGER, F., NICKLE, S. & COULSON, A. R. Proc. Nat. Acad. U.S.A. 74, 5463–5467 (1977).

---

We claim:

1. A process for the detection of cell proliferation comprising:
   a. obtaining a tissue sample from a human
   b. contacting the sample with antibodies which bind to human cyclin A; and
   c. detecting the percentage of cells containing human cyclin A in the sample, wherein an increase in the percentage of cells containing human cyclin A in the sample, compared to the percentage of cells containing human cyclin A in a normal sample, is indicative of cell proliferation.

2. The process according to claim 1 wherein the antibodies are polyclonal.

3. The process according to claim 1 wherein the antibodies are monoclonal.

4. The process according to claim 1 wherein the increase in detectable amounts of cyclin A is relative to non-proliferating (normal) cells.

5. The process according to claim 1 wherein the cell sample is a sample of tissue.

6. The process according to claim 1 wherein the detection of cyclin A is made by an ELISA method.

7. The process according to claim 1 wherein the detection of cyclin A is made by an ELISA sandwich method.

8. The process according to claim 1 wherein the detection of cyclin A is made by Western blot.

9. The process according to claim 1 wherein the detection of cyclin A is made by immunohistochemistry.

* * * * *